(12) United States Patent
Bian et al.

(10) Patent No.: US 7,585,939 B2
(45) Date of Patent: Sep. 8, 2009

(54) CHROMATIN PEPTIDES BLOCKING HUMAN HIF-1α GENE AND MODULATING THE DOWNSTREAM RELATED GENES

(75) Inventors: Xiaozhuang Bian, Dalian (CN); Chengqiu Wang, Tianjin (CN); Mi He, Wuxue (CN); Dexian Dou, Livonia, MI (US)

(73) Assignee: Geneblue Corporation, Los Angeles, CA (US)

( * ) Notice: Subject to any disclaimer, the term of this patent is extended or adjusted under 35 U.S.C. 154(b) by 389 days.

(21) Appl. No.: 11/585,544

(22) Filed: Oct. 24, 2006

(65) Prior Publication Data

US 2007/0093444 A1    Apr. 26, 2007

(30) Foreign Application Priority Data

Oct. 26, 2005    (CN) .................. 2005 1 0116615

(51) Int. Cl.
*C07K 5/00*    (2006.01)

(52) U.S. Cl. ...................................... 530/327

(58) Field of Classification Search .................. 530/327
See application file for complete search history.

(56) References Cited

U.S. PATENT DOCUMENTS 5,882,914 A * 3/1999 Semenza .................. 435/252.3

* cited by examiner

*Primary Examiner*—Stephen L Rawlings
*Assistant Examiner*—Brad Duffy
(74) *Attorney, Agent, or Firm*—Hogan & Hartson LLP

(57) ABSTRACT

Chromatin peptide drug molecules, which can block human cell hypoxia responsive pathway, are DNA affinity structural domain of related transcription genes or their imitating molecules or derivatives, containing 5-100 amino acid residues which can specifically bind firmly to HIF-1α gene self promoter or its downstream regulated more than 40 gene promoters. The above-mentioned molecules can permanently shut down molecular pathway including cell glucolysis reaction, immuno-inflammation reaction or hypoxia response, thus sustained stop uncontrollable proliferation of later stage tumor cells or chronic inflammation cells in the condition of hypoxia.

1 Claim, 1 Drawing Sheet

CHROMATIN PEPTIDES BLOCKING HUMAN HIF-1α GENE AND MODULATING THE DOWNSTREAM RELATED GENES

FIELD OF INVENTION

It belongs to the area about human genomics and malignant tumor therapy/technology using host's own system to against tumor(s). More specifically, it relates to a group of chromatin peptide molecules blocking human HIF-1α gene and its downstream related genes in the regulation pathway and their applications for preparation of tumor therapeutic drugs. Chromatin peptides, a kind of small peptides, are the degraded products of transcription factors and their bionic molecules at the length of 5-100aa. They are the fragments containing certain DNA-binding domains of transcription factors.

The chromatin peptides mentioned in this patent are the degraded products of transcription factor HIF-1α, its related transcription factors in the regulation pathway and their bionic molecules. There are homological amino acid sequences among these chromatin peptides which actually are the DNA-binding domains of these transcription factors and their related proteins. These peptides bind on the enhancers/promoters/silencers regions of their regulated genes, in turn, these peptide inhibit the binding of their corresponding transcription factors. The competitive binding remodels the function of these genes and blocks the expression of their downstream regulated genes. As the results, the following reactions are all stopped: cellular progressive proliferation/cellular glycolysis reaction, immune inflammatory reaction, vascularization reaction and the domino-like gene transcriptional regulatory cascades so that the uncontrollable proliferation of the intermediate stage and advanced cancer cells or the chronic inflammatory cells under anoxia condition is blocked for a certain period, the inflammation and acute aggravation causing proximal invasion and the vascularization reaction causing angiogenesis are terminated. Those molecules are a kind of keys which may be used to prevent and treat the uncontrollable proliferation, invasion and metastasis of malignant cancer cells.

BACKGROUND TECHNOLOGIES

In the organisms, every response is regulated at both cis- and trans-directions. The bidirectional regulation sustains the balances and the orders of vital movements of organisms. This kind of regulation is certain to concern two related modulating molecules. According to the frugal theory of organic evolution, after a molecule accomplishes the regulation of one direction, allosterism or the change of its primary structure will change and it will turn to attenuate or inhibit the reaction once promoted by it and it also becomes the modulating molecule of the other direction. These chromatin peptides and their antecedent transcription factors are mutually rivalry on functions and the molecules from same origin accomplish the bidirectional regulation at cis- and trans-directions with this mode.

Tens of thousands of people are pinched to death by malignant tumors every year, besides, some people have a closed bout with death and survive with tumor for many years and even are healed. Otherwise, more people with cancer cells in their bodies appear no symptom. It is believed that there are tens (approximately 30-100) mutated pre-cancer cells are generated in human body everyday. But those mutated pre-cancer cells are eliminated in human body everyday and endlessly. So that, those people do not get sick despite the unceasing generation of cancer cells under most conditions. The human body itself displays the inhibiting and even healing capacity of anti-cancer. After all, what kind of mode does the body use to cure many cancer patients? What is the mechanism of the cancer escaping from the control of the body and causing the death of the patients? We found that there are some chromatin peptides with bioactivity in human body and they are the DNA-binding domain fragments of some transcription factors which specifically recognize and bind with the characteristic regulatory elements/gene promoters in the process of gene transcription and activate the gene transcription; then allosterism happens and the molecules break away from the regulatory elements; when the domino-like cascade of downstream genes driven by transcription factors is constrained by some external conditions, for example, once the oxygen supply is blocked (hypoxia), the expressed transcription factors will accumulate excessively, leading to proteasome response and these factors will be degraded into chromatin peptides. Those chromatin peptides maintain the specific affinity of them with its DNA substrate, which have the capacity of binding with the regulated downstream genes and block the expression of these genes as a negative feedback. The excessive transcriptions of many proto-oncogenes which initiate tumorigenesis/aggravation all block the overexpression of their own or their downstream regulating genes through the intrinsic "broken-key blocking effect" of the organisms so that the cellular malignant proliferation are firmly blocked; maybe this is the fundamental reason causing the healing or long-term with tumor survival of many cancer patients; more patients die of cellular excessive expression caused by the continuous overexpression of those malignant genes, which may be caused by the deficient of chromatin peptides inducing "the broken-key blocking effect" to close the over-expression of those malignant genes in their bodies. Therefore, it is hopeful to make it the best way to cure cancer if we can block the over-expression of malignant genes by synthesizing and supplying these chromatin peptides or their bionic molecules and then block the cellular malignant proliferation of the tumor. Here we found some chromatin peptides possessing the functions described above.

Compared with another natural drugs generated by organism itself such as antibodies, chromatin peptides have many similarities with them, and also, they have their special functions, respectively, and serve for the health maintenance of the body and the continue of life from different aspects: antibody is a kind of protein which recognizes and binds with specific antigens of some exogenous pathogens and causes complement response, degrades and eliminates the pathogen which is harmful for the body; the body can encode more than 60 thousand kinds of antibodies aiming at different antigens through gene recombination and only a trifle of them are generously cloned and utilized: once the body is invaded by certain pathogen, the antibody will specifically recognize and bind with the antigen just as a stamp to a key, and then the cell secreting the conformal antibody which combines with the antigen in the form of lock-key mosaic structure will be cloned and utilized; thus, immune response and antibody are the professional physiological functions defending the invasion of exogenous pathogens generated during the evolution of life. Chromatin peptides are a group of oligopeptides generated by the degradation of transcription factor, recognizing and binding with the specific DNA structural domain sequences of this transcription factor itself and those downstream genes driven by it and blocking these promoters in order to block the uncontrollable expression of these genes; the cellular automatic growth and proliferation are essentially a kind of domino-like reactions related with the gene expression regulated by its chromatin template, and once the reaction network is interfered and blocked by some exogenetic and/or endogenetic factors (e.g., hypoxia without adequate supply of ATP to initiate the cellular disjunction action chain), the upstream of the gene expression cascade will accumulate excessive transcription factor and then activates the proteasome lytic response, which can degrade these junk, in which, the fragment of the transcription factor recognizing and binding with its DNA substrate, the DNA-binding domain, is reserved and binds with the DNA substrate, blocks and closes the uncontrollable gene expression cascade and the cellular growth/proliferation just like the "handle-breaking key" blocks the lock hole and prevents the other keys from opening the door. We call it "the broken-key blocking effect". Therefore, "the broken-key blocking effect" of gene transcription factor and its chromatin peptides belongs to a kind of biological function to defend the uncontrollable gene expression caused by endogenetic gene mutation generated during evolution of life. On the whole, both antibodies and chromatin peptides have the biological functions of guarding body and maintaining life: antibodies, responsible for outside, are in charge of counteracting the exogenetic invasions and decreasing the exogenetic pathogens below the tolerable level of the body; chromatin peptides, responsible for inside, are in charge of suppressing the endogenetic rebellions and inhibiting the over-expression of the malignant genes below the tolerable level of the body. Both of the two kinds of defending mechanisms are according to the mode of "gaining mastery by striking only after the enemy has struck". The immune response will not be activated and selectively clone adequate corresponding antibodies until excessive proliferation of pathogens has reached certain quantity, meanwhile, the "the broken-key blocking effect" is initiated and produces adequate chromatin peptides through the degradation only when the malignant transcription factor is excessively accumulated. However, these autochthonous defending capacities of life sometimes can not beat all enemies and maintain permanent living; supplying and enhancing the autochthonous defending capacities of life may maintain the longer livening of life through vaccination and supplement of chromatin peptides. As we all know, people controlled many lethal diseased caused by exogenetic pathogens—bacteria and viruses through vaccine injection 100 years ago. Now, we can control the endogenetic pathogen-malignant cellular diseases by supplying the related chromatin peptides.

In the last few years, considerable studies have accumulated many evidences from multiple aspects which suggest that the orgasms have obtained the above-mentioned "the broken-key blocking effect" of proteins and the chromatin peptides defending mechanism during the evolution, and the chromatin peptides, blocking the malignant cells and the malignant progressive proliferation as well as the cellular hypoxia biological response, really exist in organisms.

The relationship between the transcription factor and its derivative chromatin peptides is functional rivalry. The functional rivalry phenomenon of protein/derivative peptides includes: the promoters of HIF-1α/C-FOS/C-Myc, three promoter genes of cell proliferation, all have the histogeneous cis-transcription modulation elements (Trans-transcription modulation elements for histodifferentiation), the erythrogenic Cis-NFE2 element in HIF-1α, the B cell cytogenous Cis-MITF element in C-FOS and the T cell cytogenous Cis-NFAT element in C-Myc. It is clear that in the process of cellular development and maturation, when they initiate the functional gene group of histodifferentiation, they also block the binding site of embryonic stem cell transcription factors on the chromatin structure of HIF-1α/C-FOS/C-Myc gene transcription activity so that the chromatin phenotype is recombined and the progressive proliferation phenotype of embryonic stem cell is recombined to the kinetic equilibrium proliferation phenotype of maturity differentiated cell.

The proliferation of many malignant tumor cells may stop when they proliferate to certain quantity. Through the view of the mechanism, initiation of cell proliferation needs adequate oxygen and nutrients, however, to drive the continuous over-expression of those upstream malignant genes does not need generous energy. Therefore, hypoxia can only directly cause the arrest of the downstream proliferation genes but can not directly induce the cease of the continuous excessive transcription of the upstream malignant genes; for this reason, deficiency of energy directly leads to the arrest of the downstream proliferation genes and the terminating signal sent out by the downstream genes indirectly induces the transcription cease of the upstream malignant genes; this terminating signal is transferred and accomplished by chromatin peptides produced by proteasome response initiated by the excessive accumulation of malignant transcription factor.

The specific recognition and binding of protein/protein or protein/DNA are the basic modes of biological molecular communication activities. The combination of them is usually the combination of mosaicism among rigid structures/key-lock mode and the sequences of these domains are usually composed of hydrophobic amino acids. The hydrophobic region makes them difficult to be degraded by proteases at their dissociation state. This part of domains is also hard to approach for proteases and difficult to be degraded once they bind with each other. These structures are able to escape from the proteasome response due to these chemical characteristics of these domains, and the hydrophobic peptides also have longer half life than their complete sequence proteins which make the effective efficiency dose much lower. Otherwise, the chromatin peptides which we choose for drug treatment contain more basic amino acids, which is profit for them to get concentrated in the subacidity circumstance of tumor tissue.

The binding of regulatory subunit/domain between these two kinds of complete sequence molecules may initiate the allosterism of functional subunit and exertion of the function and then these two kinds of molecules separate with each other to achieve the dynamic functions or cis-regulation/trans-regulation functions of information transfer. Some static and long-term cis-regulation/trans-regulation phenotype combination will form as soon as the domain of a kind of degrading molecules binding with the domain of another kind of complete sequence molecules. Accordingly, the binding equilibration of chromatin peptides/transcription factor forms a type of physiological stabilized status. On the other hand, "the broken-key blocking effect" of gene expression network is a type of stabilizing effect of cellular chromatin template and growth phenotype which arrests cells at stable phenotype. Status from dynamic fluctuation to static stabilization is the dynamic equilibrium theory of cell proliferation. In summary, the cellular automatic proliferation is restrained in a limited space inside of the cells; the movements of orientation composed of two domino-like reactions between gene expression and expressed product proteins are actually a kind of switch reactions including many gene groups: a gene group is initiated and then it will be silent after action followed by the initiation of the downstream gene groups; each protein needs to degrade itself once accomplished the positive function and spares space for the later actions; sometimes it is necessary to close the expression or the function of this protein in order to enter the reaction of the next protein. So, during the long-term evolution, the organisms have constructed a kind of protein molecular mechanism which accomplish the initiation of one function and close two switch actions with "labor-saving" coordinating effect.

The traditional killing therapy aims directly at the cells in vegetative state. Virtually, many important healthy cells, including marrow, epithelial cells, etc, are all proliferating faster than some tumor cells. These therapies are all on the cost of sacrificing more healthy cells; this is the common shortage of traditional chemotherapy, radiotherapy and traditional Chinese medicine therapy. Immunotherapy and gene therapy have selectivity to act with malignant cells, particularly, the anti-vascularization reaction therapy even does not injury normal cells. The reason why the immunotherapy does not have the intended effect may be contributed to the absence of specific immunogen in tumor cells under a majority of conditions. The forthcoming studies suggest that, there is only quantitative difference but no qualitative difference between the antigens of autogenetic malignant tumors and that of normal cells. The above-mentioned gene therapy without intended effect may have chosen wrong drug target: the drug target is localized on the gene products, the dynamic mRNA or protein which immediately disappeared after the quick expression, which may only change and interfere the cellular malignant state temporarily but can not change and block its malignant phenotype permanently. The only way to change and block the cellular malignant phenotype to achieve the radical cure is to localize the drug target on the DNA level through stabilized static standard domino-like reactions and the regulatory elements of gene expression.

Now some people have realized the importance of blocking malignant genes. At present, the hot point of researches is to block malignant genes through RNAi. People have gained some effects under experimental conditions. However, there still exist some difficulties hard to overcome, including stability, permeating transportation of cellular membrane and nuclear membrane, etc so that there are great difficulties in the practical application. Some other ways blocking gene by chemicals are also difficult to apply to medical practice because of bad specificity.

Transcription factor of HIF-1α is mentioned in three comments in *Nature*, volume May, 2003, which described the hypoxia inducing factor initiating a group of genes, exerting some emergency treatment functions (Kirsty Minton THERAPEUTICS: It's suffocating in here! Nature Reviews May 2003 Vol 3 No 5): once the ischemic happened because of injury in some part of the body, firstly, it will initiate the glycolytic pathway in that tissue, like an ambulance of the body, and it will generate ATP as the energy resource under the condition without oxygen and provide the energy to the almost suffocated cells to offer relief assistance; meanwhile, it will shift the immunologic cells, including macrophages, heterophil granulocytes, etc., by biological emergency signals to eliminate dead cells and intercellular substances in order to provide living environment for those survival cells. It will also simulate the growth of the blood capillaries in the surrounding tissue to grow toward this area by biological repairing signals to transfer blood to the anoxic tissue. It is properly that that ambulance process which becomes a criminal when the tumor cells begin malignant growth and the chronic inflammation cells begin proliferating: it initiates the glycolytic pathway in tumor cells and produce ATP to assist the almost suffocated cancers cells because of hypoxia; it also calls for immune inflammatory reaction to eliminate necrosis tissue in order to provide the growth space and the chance of invasion for those survival cancer cells. Otherwise, it even leads to the growth of cancer cells to this area to supply those cancer cells with new oxygen provision and the metastasis chance. On the whole, our bodies have not generated the intelligence to clearly distinguish right and wrong during evolution: the ambulance, initiated by HIF-1α transcription factor, not only assists the injury of normal tissue but also assist those tumor cells to escape from the suffocating state caused by the above-mentioned chromatin peptides "broken-key blocking effect" without hesitation and leads to the pathogenetic condition aggravation and death of some cancer patients.

Under what kind of conditions does the malignant proliferation of tumor cells initiate the blocking effect of chromatin peptides and achieve the self-healing of the body, and under what kind of conditions does it fail to initiate the blocking effect and escape from the control of the body? Oxygen is the first restriction factor of cell proliferation: during cell proliferation, the cell density increases in the limited space with the increase of cell population and the provision of oxygen and glucose decreases by and by so that the cell proliferation slows down till stops. In short, the relationship between the capacity of cell proliferation and the cell population is inverse proportion and the final proliferation and blocking may give out a determined cell population and the size of tumor tissue. The typical physiological case is skin: basal cells, the most inner layer of skin, are close to vessels, obtain adequate oxygen and proliferate toward the exterior by and by, and the speed of proliferation slows down with the decrease of oxygen till the end cell of epidermis, which stop splitting because of oxygen deficiency and enter the necrosis state with karyopyknosis.

The typical pathological case is hypoxia of tumor: mutations of some signal genes lead the cells to escape the control of outside signals, for example, the loss of contact inhibition, and the cells will continuously proliferate, and they will stop proliferating or enter the apoptotic state or enter resting state when the oxygen decreases to a critical point. The molecular mechanism of the cell proliferation blocking caused by the above-mentioned minimum critical point of oxygen is probably as following: the transcription factors of MYC group initiate their downstream cell proliferation gene group and promote the domino-like reactions of the downstream cell proliferation genes and set them onto the cell division pathway, and the reaction will cease once the oxygen reduce to a critical point; the transcription factors of MYC group will induce/activate proteasome response once they are accumulated to a maximal critical point, which will degrade these cell proliferation initiating molecules and those cellular apoptosis related shutting off molecules into chromatin peptides in order to block the expression of these cell proliferation promoting transcription factors. If "the broken-key blocking effect" of MYC group drops out "the broken-key blocking effect" of HIF-1α group will restrict the nutrient and energy provision of tumor cells. The outcome of long-term human evolution makes the body have multistrata and multipath capacity to resist the uncontrollable proliferation of malignant cells and this is the mechanism of system autogenetic-healing. The chromosome mutation or gene mutation in some tissue cells will induce the dropout of HIF-1α hypoxia inducing pathway and the cellular malignant proliferation, invasion and metastasis will escape from the blocking caused by asphyxiant chromatin peptides through the following HIF-1α dropout steps: first of all, HIF-1α switches on the glycolytic pathway of tumor cells, which increases the resistance of cells to hypoxia circumstances and makes the tumor move into the in situ progressive proliferation step; subsequently, it induces the immune inflammatory reaction to eliminate the necrotic tissue and provides the living space and the chance of invasion for those survival cancer cells, which makes the tumor move into the in situ invasion stage; finally, it even induces the growth of blood vessels toward the cancer tissue to provide new oxygen provision and the chance of invasion for those cancer cells, which makes the tumor move into the heterotopic metastasis and rapid aggravation stage. The initiation and blocking of these cellular malignant proliferations are both accomplished through cell proliferation promoting transcription factor and the chromatin peptides produced by its degradation in "the broken-key blocking effect". The chromatin peptides produced through transcription factors of MYC group and those chromatin peptides produced through transcription factors of HIF-1α group block the cellular malignant genesis and metastasis and alleviate the cellular malignant proliferation, invasion and metastasis.

It is especially necessary to point out that there exists large difference on the nutrient and energy provision and requirement between malignant tumor cells and normal cells. Some data suggest that the cell needs much more energy and nutrients to grow than to maintain its activity. However, the malignant cancer cell needs much more nutrient and energy than normally growing cells because of its much faster uncontrollable growth rate. Judah Folkman, a famous surgeon, found that the genesis of malignant tumor is followed by angiogenesis of large quantity of blood vessels and it is one of the ways for tumor cells to enlarge their oxygen provision in order to increase the energy and nutrient provision. On the other hand, the malignant cell initiates anaerobic metabolism—glycolytic pathway and increases the permeation speed of oxygen and glucose through the cellular membrane and blood vessel to retrieve the deficiency of oxygen and energy. Folkman proposed the conception of anti-angiogenesis therapy, which relies on confining the oxygen and energy provision of malignant tumor cells. However, some drug target of present anti-angiogenesis therapy is angiogenin, a gene product for stimulating angiogenesis; some proteins inhibiting tumor angiogenesis, for example, Endostatin, Angiostatin, etc., mainly produce a marked effect through the rivalry with angiogenesis stimulating factors, for example, VEGF. Those therapies do not cut off the origins of angiogenin or VEGF— the encoding genes of that, making it necessary to continuously complement anti-angiogenesis materials.

The patient's pathogenetic condition will get worse till death once the proliferation and metastasis of tumor cells lose control. For this point of view, no matter how aggravated has the patient's pathogenetic condition been, it may be stabilized and the patient's life may be saved so long as you block the cellular malignancy pathway by the chromatin peptides obtained from the degradation of transcription factors such as HIF-1α On the other hand, there are some other mechanisms of the initiation of cellular malignant proliferation besides HIF-1α pathway. However, the malignant growth of any entity tumor must break through the restriction of energy and nutrient. Therefore, the expression of HIF-1α transcription factor and its regulating transcription factors are necessary for the malignant growth of any entity tumor. With regard to the tumor malignant growth caused by the breakthrough of the oxygen restriction leaded by HIF-1α and anchoring-dependent and contact inhibition pathways regulated by MYC group, the blocking agents we designed can not only realize the cellular phenotype transformation from malignant phenotype to normal cellular phenotype but also lead to the death or apoptosis of tumor tissue because of absence of oxygen and energy. According to those malignant tumors caused by the other mechanisms, it mainly induces the death or apoptosis of cancer cells by the restriction of nutrient, oxygen and energy.

To sum up, we described the function of HIF-1α, a hypoxia restriction factor, in human body and its function during the genesis of malignant tumor; and analyzed the functional antagonism between chromatin peptides, produced by the degradation of the related transcription factor, and their derivative precurosors and "the broken-key blocking effect" produced by the binding between chromatin peptides and the silencer/enhancer/promoter of the gene chromosome plate. On these foundations, we have tested chromatin peptides as the drug treating symptoms and getting at the root to cure malignant tumors and carried out a serial of trials to verity their pharmacodynamic actions and safety.

CONTENTS OF INVENTION

Figure 1:
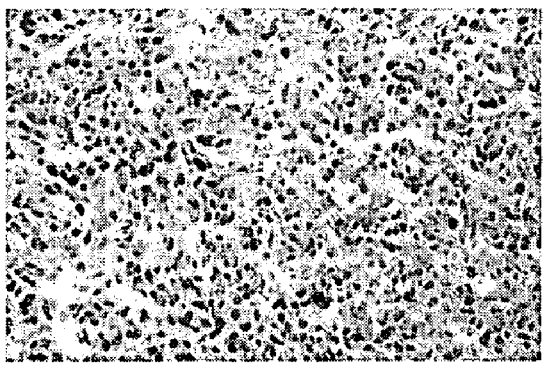
FIG. 1(A) is the observation of tumor tissue treated with water (control).
FIG. 1(B) is the observation of tumor tissue treated with chromatin peptide drug.
Figure 1:
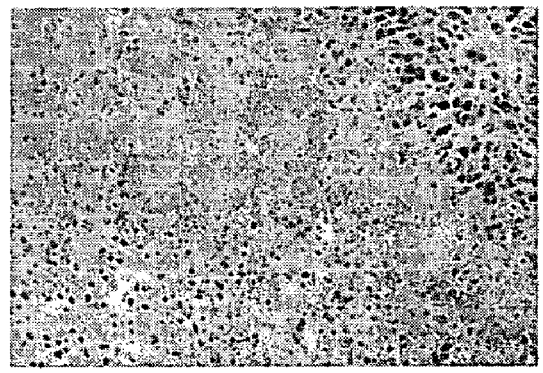

The chromatin peptides referred in this invention are substantially oligopeptides, produced by the derivation/degradation of transcription factors which initiate the domino-like gene expression activities of driving cellular glycolysis response, immune inflammatory reaction and vascularization reaction response, and their bionic molecules; these transcription factors initiate the malignant proliferation, inflammation and vascularization reaction of tumor cells and then cause the malignant growth, invasion and metastasis of cancer cell. But the chromatin peptides produced by the derivation/degradation of them block the malignant growth, invasion and metastasis of these tumor cells which leads to the endless realization of "autogenetic healing without treatment" in many cancer patients; this technology including a few kinds of chromatin peptides and their derivates screened out of human genome data base, they can block proto-oncogenes and cut off the energy provision of cancer cells which leads to the death or apoptosis of them; or transform the cellular phenotype of malignant tumors. These chromatin peptides may be applied to the prevention and treatment of various human malignant tumors (including marrow fluid malignant tumors). These chromatin peptides, as the bionic medications, are candidates of drugs with biological activities of prevention and curing of malignant tumors.

Therefore, the purposes of this invention are to provide:

1. A kind of chromatin peptides molecules which can block hypoxia response pathway in human cancer cells, and these molecules are DNA-binding domain sequences of the related transcription factors and their bionic molecules or derivates, composed of 5-100 amino acids, and they can specifically and firmly bind with the promoter of HIF-1α gene or the promoters of its more than 40 downstream genes driven by the transcription factor expressed by it. These above-mentioned molecules may cause the long-term blocking of the molecular pathway of the following cellular hypoxia responses: cellular glycolysis response and/or immune inflammatory reaction and/or vascularization reaction response so that they may block the uncontrollable proliferation of the cells in intermediate stage and terminal cancers and chronic inflammation under anoxia conditions for a long time, which induces the inflammatory reaction causing the proximate invasion of cancer cells and the vascularization reaction response causing the distant metastasis, in order to achieve the purpose of preventing and/or treating the malignant and uncontrollable proliferation, invasion and metastasis of cancer cells.

2. According to the chromatin peptides molecules mentioned in item 1, one or more kinds are chosen out of peptides 1-21 in the Table 2.

3. According to the chromatin peptides medicine molecules mentioned in item 2, the peptides or peptide derivates at the length of 3-100 amino acids, which contain at least 3 amino acids homologous sequences with any one of the 21 chromatin peptides mentioned in item 2, can block the DNA-binding domain of gene HIF-1α or its related intermediate/down stream genes.

4. According to the chromatin peptides mentioned in any item of the above 1-3 items, the trans-chromatin peptides with any amino acid sequence, used to bind and block the HRE regulatory element of HIF-1α gene and its related genes, should be composed of 5-100 amino acids.

5. According to the chromatin peptides mentioned in any item of the above 1-3 items, the trans-chromatin peptides with any amino acid sequence, used to bind and block the XRE elements of HIF-1α gene and its related genes, are composed of 5-100 amino acids.

6. According to the chromatin peptides mentioned in any item of the above 1-3 items, the trans-chromatin peptides with any amino acid sequence, used to bind and block the related genes in the regulating network of HIF-L a transcription factor, are composed of 5-100 amino acids.

7. All derivates of these chromatin peptides obtained through the amino acid deletion or addition of the 21 sequences of chromatin peptides or all chromatin peptides with the minimum 3-amino acid homological structure mentioned in item 2 which can block the cellular hypoxia response pathway, or the derivates of chromatin peptides obtained through the modification of their end- or side chain radicals. These derivates can improve the cellular membrane permeability and nuclear membrane permeability, change the half life and stability of medicine and improve the ability of blocking cellular hypoxia response of these chromatin peptides.

8. The medicine complexes which are composed of one or many chromatin peptides or their derivates with pharmaceutical dosis efficacy mentioned in any item of above 1-7 items and the randomly chosen pharmaceutical acceptable vector.

9. The applications of these chromatin peptides or their derivates or the complexes containing them mentioned in any item of above items 1-7 in the treatment of human malignant tumors or animal malignant tumors.

10. According to the medicine complexes mentioned in item 8, they may use by injection, oral application capsules, and slow-releasing system.

11. According to the chromatin peptides or their derivates mentioned in any item of above items 1-7, their characteristics lies on their binding ability with the hypoxia response element HRE (hypoxia responsive element) 5'-[AG]CGTG-3' of anyone or many of the following 6 Trans-transcription factors: HA/PAS/NPA1/SIM1/SIM2/NPA3; or binding with XRE (xenbiotic responsive element) 5'-caCGTGct-3' of anyone or many of the following 5 Cis-transcription factors: ARNT/ARN2/BMAL/CLOC/NPA2.

The impacting mediums acting on intermediate/downstream regulatory elements of HIF-1α gene may be obtained by analyzing the cistron of regulatory element of HIF-1α protein transcription factor, and the bionic molecules may be obtained by using random peptide technology and analyzing the structures of these natural impacting mediums.

The impacting mediums acting on intermediate/downstream regulatory elements of HIF-1α gene—chromatin peptides drug molecules can block the DNA-binding domain of cellular hypoxia response pathway.

The impacting mediums acting on intermediate/downstream regulatory elements of HIF-1α gene—chromatin peptides medicine molecules have high degree of specificity and they do not affect the activity of any other gene except blocking Hα gene and its intermediate/downstream related genes, otherwise, their DNA-binding domains have much higher affinity to gene HIF-1α and its intermediate/downstream related genes compared with the affinity of DNA-binding domain of the allelomorphic gene in normal cells.

These drug molecules can permeate through cellular membrane and nuclear membrane and arrive their targets. Therefore, they can be administered by intramuscular injection, intravenous injection, skin permeation, intravenous transfusion pathway, tumor in situ injection and capsule oral application. The dosage depends on the patient's specific condition, for example, body weight, age, specific disease and pathogenetic condition. It also depends on the physician's clinical experience. However, it usually is 0.005-30 mg/day and may take once or divide into multiple dosing.

These drug molecules are not modified and can not resist the digestion and hydrolysis of gastric acid and pepsin so that they can not directly be taken orally. But they can oppose the digestion and hydrolysis of gastric acid and pepsin after the chemical modification of their end and side chains and then they may be administered orally.

By blocking HIF-1α gene and its middle/downstream related genes, these drug molecules confine or fully prohibit inflammatory reaction around the malignant tumor cell, and prohibit malignant cells infiltrating to the surrounding tissue induce by inflammatory reaction.

By blocking HIF-1α gene and its middle/downstream related genes, these drug molecules can terminate malignant cells stimulating vascularization reaction and slow down or stop malignant cells immediate proliferation inducing rapid aggravation and blood mediating metastasis.

These drug molecules are safe for human body and do not influence normal metabolism of organs and tissues, renew of tissues and cells as well as human growth and development.

These drug molecules can be used in treating and preventing different mechanisms initiated entity origin malignant tumors which include myeloma and entity origin fluid malignant tumors, such as T lymphocytic leukemia and B cell leukemia.

These drug molecules can be obtained through oligopeptide chemosynthesis, genetic engineering bacteria zymotechnics, animal gene engineering and transcription factor enzyme digestion method. All these methods are known by the ordinary technologists of this field.

This invention includes a kind of medicine molecules blocking Hα gene and the related gene in its regulation network. These molecules can be prepared into various kinds of dosage form of drugs. It has been used in preventing and treating all kinds of and stages entity original malignant disease through intravenous injection, skin diffusion, intramuscular injection and oral administration, etc. Giving these natural molecules and bionic molecules can enhance the clearance capability of human body to malignant cells, achieve the aim of not hurting normal cells, tissues and organs, and slow down malignant or cure cancer thoroughly and permanently.

The drug molecules designed in this patent include chiefly through response transcription factor fuzzy grouping analysis on three functions (cellular glycolysis reaction, immune inflammation reaction and vasculogenesis reaction) genetic group (more than 40 genes) regulatory element which bind hypoxia, and retrieve genetic group pooling upstream transcription factor named HIF-1α, this transcription factor is hypoxia response protein phylogen, which accept regulation by oxygen and temperature, and make cells shift from aerobic response phenotype to hypoxia response phenotype, thus lead to malignant cell proliferation, invasion and metastasis.

The present invention also contains two kinds of HIF-1α related transcription factors indexed from gene banks, altogether 11. One kind are 6 Trans-transcription factors (HA/PAS/NPA1/SIM1/SIM2/NPA3) bind with HRE (hypoxia responsive element) 5'-[AG]CGTG-3', the other are five Cis-transcription factors (ARNT/ARN2/BMAL/CLOC/NPA2) bind with XRE (xenbiotic responsive element) 5'-caCGTGct-3'. HRE group and XRE group transcription factors cooperate with each other, with genesis or isogenesis composite elements formed between them, each responsible for Trans- or Cis-regulation of gene transcription. Trans-transcription factors on HRE element can promote gene transcription, while Cis-transcription factors on XRE elements may block gene transcription.

This invention also includes the above 11 HIF-1α related transcription factor degraded derivative chromatin peptides and 13 bionic molecules, all together 24 drug molecules, three of which have identical amino acid sequences, so actually there are 21 medicine molecules(see sequence Table 1, Table 2). Whether they are derived by Trans-regulation transcription factors or Ci-regulation transcription factors, and whether natural or the bionic molecules of these natural, all of them can be employed to close hypoxia response functional pathway. We named HRE element and XRE element chromatin peptide as CPHTrans-n (Chromatin Peptide of Hα Trans-Regulation) and CPHCis-n (Chromatin Peptide of Hα Ci-Regulation), respectively. The basis of our designed chromatin peptide molecules, and the nomination of chromatin peptide drug target sites and chromatin peptides deviated prosoma see Table 1.

Table 1 derivative chromatin peptides of HIF-1α degraded by related transcription factor and drug molecules and target sites of derivative chromatin peptides

TABLE 1 derivative chromatin peptides of HIF-1α degraded by related transcription factor and drug molecules and target sites of derivative chromatin peptides

| Chromatin Peptides | Precursors Transcription factors | Biological functions and use for certain syndromes |
|---|---|---|
| CPHTrans-1 | HIF-1α | Functions as a master transcriptional regulator of the adaptive response to hypoxia. |
| Target | | HRE (hypoxia response element) 5'-[AG]CGTG-3' //acgctcaCGTGct (−307–295) (SEQ ID NO: 1) Under hypoxic conditions activates the transcription of over 40 genes, including, erythropoietin, glucose transporters, glycolytic enzymes, vascular endothelial growth factor, and other genes whose protein products increase oxygen delivery or facilitate metabolic adaptation to hypoxia. Plays an essential role in embryonic vascularization, tumor angiogenesis and pathophysiology of ischemic disease. |
| Sequence | | 14aa Arg Arg Lys Glu Lys Ser Arg Asp Ala Ala Arg Ser Arg Arg (SEQ ID NO: 2) (SEQ ID NO: 2) 10aa HRE Domain Arg Lys Glu Lys Ser Arg Asp Ala Ala Arg (SEQ ID NO: 3) |
| CPHTrans-2 | PAS1 | Regulates the vascular endothelial growth factor (VEGF) expression and seems to be implicated in the development of blood vessels and the tubular system of lung. |
| Target | | HRE (hypoxia response element) 5'-[AG]CGTG-3' //acgctcaCGTGct (−307–295) (SEQ ID NO: 1) Activation seems to require recruitment of transcriptional coactivators such as CREBPB and probably EP300. Interaction with redox regulatory protein APEX seems to activate CTAD. |
| Sequence | | 13aa Arg Lys Glu Lys Ser Arg Asp Ala Ala Arg Cys Arg Arg (SEQ ID NO: 4) 10aa HRE Domain Arg Lys Glu Lys Ser Arg Asp Ala Ala Arg (SEQ ID NO: 5) |
| CPHTrans-3 | SIM1 | Transcriptional factor that may have pleiotropic effects during embryogenesis and in the adult |
| Target | | Efficient DNA binding requires dimerization with another bHLH protein. Heterodimer of SIM1 and ARNT. |
| Sequence | | SIM1 13aa Met Lys Glu Lys Ser Lys Asn Ala Ala Arg Thr Arg Arg (SEQ ID NO: 6) 9aa HRE Domain Lys Glu Lys Ser Lys Asn Ala Ala Arg (SEQ ID NO: 7) |
| CPHTrans-4 | SIM2 | It may have pleiotropic effects in the tissues expressed during development. |
| Target | | EFFICIENT DNA BINDING REQUIRES DIMERIZATION WITH ANOTHER BHLH PROTEIN. HETERODIMER OF SIM2 AND ARNT. Transcription factor that may be a master gene of CNS development in cooperation with Arnt. |
| Sequence | | SIM1 13aa Met Lys Glu Lys Ser Lys Asn Ala Ala Arg Thr Arg Arg (SEQ ID NO: 6) 9aa HRE Domain Lys Glu Lys Ser Lys Asn Ala Ala Arg (SEQ ID NO: 7) |
| CPHTrans-5 | NPA3 | May plays a broad role in neurogenesis |
| Target | | XRE Efficient DNA binding requires dimerization with another bHLH protein. |
| Sequence | | NPA3 17aa Arg Lys Glu Lys Ser Arg Asp Ala Ala Arg Ser Arg Arg Gly Lys Glu Asn (SEQ ID NO: 8) 10aa HRE Domain Arg Lys Glu Lys Ser Arg Asp Ala Ala Arg (SEQ ID NO: 9) |
| CPHTrans-6 | NPA1 | Neuronal PAS domain protein 1 |
| Target | | Contains 2 PAS (PER-ARNT-SIM) dimerization domains Contains 1 PAS-associated C-terminal (PAC) domain. |
| Sequence | | NPA1 13aa Arg Lys Glu Lys Ser Arg Asn Ala Ala Arg Ser Arg Arg (SEQ ID NO: 10) 10aa HRE Domain Arg Lys Glu Lys Ser Arg Asn Ala Ala Arg (SEQ ID NO: 11) |
| CPHCis-7 | ARNT | |
| Target | | XRE (XENOBIOTIC RESPONSE ELEMENT) 5'-acgctcaCGTGct-3' (−310–298) (SEQ ID NO: 1) The heterodimer with HIF1A or EPAS1/HIF2A functions as a transcriptional regulator of the adaptive response to hypoxia. Required for activity of the Ah (dioxin) receptor. This protein is required for the ligand-binding subunit to translocate from the cytosol to the nucleus after ligand binding. |

TABLE 1-continued derivative chromatin peptides of HIF-1α degraded by related transcription factor and drug molecules and target sites of derivative chromatin peptides

| Chromatin Peptides | Precursors Transcription factors | Biological functions and use for certain syndromes |
|---|---|---|
| Sequence | | 13aa Ala Arg Glu Asn His Ser Glu Ile Glu Arg Arg Arg Arg (SEQ ID NO: 12) 9aa XBE Domain His Ser Glu Ile Glu Arg Arg Arg Arg (SEQ ID NO: 13) |
| CPHCis-8 | ARN2 | EFFICIENT DNA BINDING REQUIRES DIMERIZATION WITH ANOTHER BHLH PROTEIN. HETERODIMER WITH THE ARYL HYDROCARBON RECEPTOR (AHR) OR THE SIM1 PROTEIN. |
| Target | | XRE (XENOBIOTIC RESPONSE ELEMENT) 5'-acgctcaCGTGct-3' (−310-298) (SEQ ID NO: 1) SPECIFICALLY RECOGNIZES THE XENOBIOTIC RESPONSE ELEMENT (XRE). |
| Sequence | | 13aa Ser Arg Glu Asn His Ser Glu Ile Glu Arg Arg Arg Arg (SEQ ID NO: 14) 9aa XBE Domain His Ser Glu Ile Glu Arg Arg Arg Arg Arg (SEQ ID NO: 15) |
| CPHCis-9 Target | BMAL | Brain and muscle ARNT-like 1 XRE (3'-cacgtg-5') CLOCK-BMAL1 heterodimers bind to an E-box element (3'-cacgtg-5'), thereby activating transcription of PER1, and possibly of other circadian clock proteins. Efficient DNA binding requires dimerization with another bHLH protein. Forms an heterodimer with CLOCK. Interacts with HSP90; with AHR in vitro, but not in vivo. |
| Sequence | | 13aa Ala Arg Glu Ala His Ser Glu Ile Glu Lys Arg Arg Arg (SEQ ID NO: 16) 9aa XBE Domain His Ser Glu Ile Glu Lys Arg Arg Arg (SEQ ID NO: 17) |
| CPHCis-10 Target | CLOC | CIRCADIAN REGULATOR XRE (3'-CACGTG-5') CIRCADIAN REGULATOR THAT ACTS AS A TRANSCRIPTION FACTOR. CLOCK-BMAL1 HETERODIMERS BIND TO AN E-BOX ELEMENT (3'-CACGTG-5'), HEREBY ACTIVATING TRANSCRIPTION OF PER1, AND POSSIBLY OF OTHER CIRCADIAN CLOCK PROTEINS. MUTANT CLOCK AND BMAL1 FORM HETEREODIMER THAT BIND DNA, BUT FAIL TO ACTIVATE TRANSCRIPTION |
| Sequence | | 13aa Lys Arg Val Ser Arg Asn Lys Ser Glu Lys Lys Arg Arg (SEQ ID NO: 18) 9aa XBE Domain His Ser Glu Ile Glu Lys Lys Arg Arg (SEQ ID NO: 19) |
| CPHCis-11 Target | NPA2 | Neuronal PAS domain protein 2 EFFICIENT DNA BINDING REQUIRES DIMERIZATION WITH ANOTHER BHLH PROTEIN. INTERACTS WITH HSP90. Contains 2 PAS (PER-ARNT-SIM) dimerization domains Contains 1 PAS-associated C-terminal (PAC) domain. |
| Sequence | | NPA2 13aa Lys Arg Ala Ser Arg Asn Lys Ser Glu Lys Lys Arg Arg (SEQ ID NO: 20) 9aa XBE Domain Arg Asn Lys Ser Glu Lys Lys Arg Arg (SEQ ID NO: 21) |
| CPHCis-12 | AHR | Involved in cell-cycle regulation. Likely to play an important role in the development and maturation of many tissues. |
| Target | | AHR promoter In the nucleus, heterodimer of AHR and ARNT. Interacts with coactivators including SRC-1, RIP140 and ERAP 140, and with the corepressor SMRT. |
| Sequence | | 28aa Arg Lys Arg Arg Lys Pro Val Gln Lys Thr Val Lys Pro Ile Pro Ala Glu Gly Ile Lys Ser Asn Pro Ser Lys Arg His Arg (SEQ ID NO: 22) |

We found that there are 10 amino acids homology domain NH2-Arg Lys Glu Lys Ser Arg Asp Ala Ala Arg-COOH (SEQ ID NO: 10) binding with HA/PAS/NPA1/SIM1/SIM2, five trans-transcription factor on HRE element. In addition, there is also 12 amino acids homology region, NH2-Lys Glu Lys Ser Lys Asn Ala Ala Arg Thr Arg Arg-COOH (SEQ ID NO: 23). These homology series together with same-length structural domain and their derivative oligopeptide sequence consist of drug molecule sequences are designed.

We also found that six Cis-transcription factors (ARNT/ARN2/BMAL/CLOC/NPA2/AHR) on HRE element have 9 amino acids homology domain, NH2-His Ser Glu Ile Glu Arg Arg Arg Arg-COOH (SEQ ID NO: 14), and 12 amino acids length structural domain, NH2-Arg Glu Ala His Ser Gln Ile Glu Lys Arg Arg Arg-COOH (SEQ ID NO: 24). These homology series together with same-length structural domain and their derivative oligopeptide sequence also belong to the drug molecule sequences are designed.

The drug molecules designed in this invention have definite target sequence. Besides binding with regulatory domain silencer, promoter and enhancer of HIF-1α gene, the binding sites of these drug molecules also exist in intermediate and downstream associated genes related to the transcription factor HIF-1α in regulation network.

The work of active chromatin peptides blocking HIF-1α gene and the related genes in its regulation network begins with an analysis of gene transcriptional regulatory cascades supporting a certain biological function response. This gene transcriptional regulatory cascades theory presumed that any biological function response be realized by domino-like transcriptional regulatory cascades, which consist of related transcription factors. The upstream factors bind with regulatory element of downstream factors to promote expression of downstream protein transcription factors, meanwhile, every transcription factor can bind with promoter, silencer, or enhancer of the encoding gene itself, thus after several layer linkage of transcription factors, finally promote coordinate expression and the function of functional gene group.

Although the molecular basis of malignant tumor cells is very complicated, uncontrollable proliferation, a simple and standard definition, is proper for all kinds of malignant tumors. Whereas the proliferation and renew of benign cells were regulated by microenvironment around the body, and the normal cells are controlled by the body or other cells through three protein functional pathways, which are respectively controlled by direct contact communication, indirect molecular communication and oxygen/nutrition provision. These three molecular pathways are regulated by individual cell phenotype transfer molecule and Phylogen C-Myc/C-FOS/Hα, and the downstream of the three different cell proliferation protein network connect to cell proliferation/differentiation/apoptosis functional gene groups, while their upstream are promoted or stopped by various tissues/organs genetic Trans-transcriptional regulatory factors and histodifferentiated Cis-transcriptional regulatory factors.

The relationship between control of HIF-1α pathway—oxygen and nutrient substances and malignant tumors: the regeneration and proliferation of cells need more oxygen and nutrient than general metabolism, with sufficient blood supply, can histocytes grow and develop thoroughly. The skin epidermal cells and malignant tumor centrocytes may stop proliferation and begin apoptosis due to short of blood and oxygen supply. Many early carcinoma patients can cure with treatment may attribute to this body control. Recent studies found that the malignant cells in the terminal cancer patients escape from this control to in situ malignant proliferate, infiltrate and heterotopia transfer. The body oxygen control exit escaping these cell proliferations was transcription factor HIF-1α, which was called hypoxia-inducible factor. Under the normoxic condition, HIF-1α is hydroxylated and bind with proteinV of ubiquitin linkage multienzyme complex, which finally causes ubiquitinization of HIF-1α leading to degradation. The hydroxylation of HIF-1α is inhibited under hypoxia condition. HIF-1α is used to promote transcription of more than 40 genes, including three functional reaction pathways of erythropoietin (EPO), glucose transport factor, glycolytic enzyme and vascular endothelial growth factor inducing cell growing under hypoxia condition. Firstly, induce glucolysis reaction without oxygen to obtain ATP energy molecular, which results in the tolerance of malignant cells to hypoxia condition and they can proliferate malignantly under hypoxia condition. Secondly, induce immune inflammatory reaction. The malignant cells with glucolysis reaction send out signal to guide inflammatory cells metastasis to their domain, and these signals induce inflammatory cells including macrophagocytes and neutrophil transfer from circulation system to hypoxia tumor tissue surroundings. This reaction leads to inflammatory cells remove necrosis cells around the tumor, which results in survival malignant cells infiltrating to surroundings. Thirdly, induce vascularization reaction. The hypoxia malignant cells send signals to periphery blood capillary tissue to guide them grow to the lump area, and provide malignant cells with blood. This reaction leads to malignant cells obtaining oxygen and nutrients, thus transfer to heterotopia through blood vessel.

The breakup of cellular oxygen supply regulation network results in un-sequence uncontrollable expression of HIF-1α and its related genes, inducing malignant cells to escape body control pathway. Superficially, it is initiated by breakup of protein effective network/cascade, actually, if this breakup is only caused by temporary defect of protein/oxygen, not by DNA defect, then, this breakup just leads to cells temporarily enter proliferation. When proliferation and differentiation complete, gene transcriptional regulatory cascade will be regulated and recovered to normal chromatin peptide form in individual development, and the driven cells return to non-proliferative state. Then malignant cells can produce and continually maintain their malignant/progressive proliferation due to the defect of above-mentioned chromatin peptide orbit. When cells get proliferation, the upstream transcription factors do not promote cell functional metabolism gene group transcription cascade, but promote the transcription cascade of above-mentioned cell proliferation control gene group, thus leads cells to proliferation pathway.

In fact, most malignant cells development is related to the defect of some protein or gene (usually called tumor-suppressing gene) on the package phenotype cellular normal genetic transcription tunnel, which induced genetic transcription depart from the orbit. Opposite to facialis phenomenon, malignant cells escaping body control starts from the expression of above-mentioned cell proliferation control network protein abnormal time and over dose, and then driven by cell malignant superiority alternative law and the following related branching factor transcription feedback flywheel mechanism, the malignization gained sustain and acceleration. So the result is, malignant proliferation of tumors does not escape from protein effective orbit but escapes from Cis-protein binding DNA or chromatin orbit, only by using Cis-protein/or DNA binding protein to block and repair the pathway, can it effectively inhibit malignant protein overexpression and malignant cells uncontrollable proliferation, through which it can get at the root of malignant tumor. Thus, microgenetic transcriptional regulatory cascade has driven and maintained protein effect regulatory cascade, and then showed macrocell proliferation appearance. The molecule pathway of cell proliferation includes genetic transcriptional regulatory pathway regulated by DNA or chromatin Cis-regulated orbit upstream and protein effective regulatory way driven by genetic pathway.

The pathogenesis of human tumor is very complicated and many genes are associated with tumor. Now we summarized that there exist three ways for the mechanisms of the cellular disordering proliferation to escape from the C-Myc/C-FOS/Hα regulation pathway. Maybe there are some other mechanisms causing the disorder of cell proliferation. To block HIF-1α and the downstream genes of its regulation network can control the proliferation of the uncontrollable entity cells from various origins for different mechanisms. First, it directly blocks the cellular disordering proliferation caused by escaping the regulation through HIF-1α pathway; Secondly, the malignant proliferation and metastasis of entity tumor from various origins may activate the overexpression of HIF-1α and then it will activate the anaerobic glycolysis to provide energy for the cancer cells. Activate inflammation which provides the anchoring place and space for those malignant cells, and to stimulate angiogenesis which causes rapid aggravation and metastasis. Reconstruction of HIF-1α gene behavior with chromatin peptide drug moleculars can cut off anaerobic glycolysis pathway, control over inflammatory reaction around the lump, as well as inhibit blood vessel grow forward malignant lumps, thus relieve or thoroughly inhibit tumor tissues' proliferation, invasion and metastasis. Therefore, blocking HIF-1α gene and its related gene's chromatin peptide gene impacting medium has extensive effect to all kinds of entity tumors.

The chromatin peptide medicine molecules we designed have longer half life than common oligopeptides. Animal experiment indicated that administer these chromatin peptide by injecting at tumor around sites or in vein, it has obvious inhibitory action to human mammary cancer cell strain0404 MDA-MB-435, human colon carcinoma cell strain HCT etc. transplanted BALB/c-nu tumor and animal tumor cell strain S-180 transplanted Kunming mouse tumor, and pathological section has showed quantity of cancer cells apoptosis at the center of medication treated tumor samples (see practice Samples). Theoretically, chromatin peptide medicine molecule can not permanently block the related cancer producer genes. We suggest that due to human personal body intellect, under many circumstances human body may clean up malignant cells by itself. Cancer patients feel ill with cancer because of defecting of protection mechanism in vivo. However, the defection can be recovered. Our designed chromatin peptide medicine molecules can make most malignant cells death on the one hand; on the other hand, it can complete the phenotype transformation of malignant cells. If these medical molecules can be continued to be used, it can significantly decrease malignant cell population in vivo. Thus, firstly, malignant cell population in vivo has been decreased to the limitation which can be cleaned up; secondly, owing to the controlled malignant cell proliferation, human immune, metabolism and organ and organization function will be recovered and strengthened, as well as enhance monitoring and clearance ability of human body to malignant cells. The most important thing is that it strives time and opportunity for human body to deal with the malignant proliferation activity.

By index and analysis on human gene bank, we designed and validated chromatin peptide impacting medium which can block transcription factor HIF-1α encoding gene and associated intermediate and downstream transcription factor encoding genes, as well as detect a certain of base sequence position blocked by impacting medium, as shown in Table 1, Table 2.

TABLE 2

The amino acid sequences and target sites of the chromatin peptides capable of blocking HIF-1α and its related transcription factor genes

| Chromatin peptide # | Amino acid sequnce | Target |
|---|---|---|
| 1 | 10aa Arg Lys Glu Lys Ser Arg Asp Ala Ala Arg-COOH | HIF-1α regulated HRE (hypoxia response element) 5'-[AG]CGTG-3'///ACGCTCACGTGCT (−307–295) The binding sites of transcription factor HIF-1α in its related genes |
| 2 | 12aa Lys Glu Lys Ser Lys Asn Ala Ala Arg Thr Arg Arg-COOH | HIF-1α regulated HRE (hypoxia response element) 5'-[AG]CGTG-3' //ACGCTCACGTGCT (−307–295) The binding sites of transcription factor HIF-1α in its downstream regulated gene |
| 3 | 14aa Arg Arg Lys Glu Lys Ser Arg Asp Ala Ala Arg Ser Arg Arg-COOH | HIF-1α regulated HRE (hypoxia response element) 5'-[AG]CGTG-3' //ACGCTCACGTGCT (−307–295) The binding sites of transcription factor HIF-1α in its downstream regulated gene |
| 4 | 13aa Arg Lys Glu Lys Ser Arg Asp Ala Ala Arg Cys Arg Arg-COOH | HIF-1α regulated HRE (hypoxia response element) 5'-[AG]CGTG-3' //ACGCTGACGTGCT (−307–295) HIF-1α binding site in PAS1 gene |
| 5 | 10aa Arg Lys Glu Lys Ser Arg Asp Ala Ala Arg-COOH | HIF-1α regulated HRE (hypoxia response element) 5'-[AG]CGTG-3' //ACGCTCACGTGGT (−307–295) HIF-1α binding site in PAS1 gene |
| 6 | 13aa Arg Lys Glu Lys Ser Arg Asn Ala Ala Arg Ser Arg Arg-COOH | HIF-1α regulated HRE (hypoxia response element) 5'-[AG]CGTG-3' //ACGCTCAGGTGCT (−307–295) HIF-1α regulated |
| 7 | 17aa Arg Lys Glu Lys Ser Arg Asp Ala Ala Arg Ser Arg Arg Gly Lys Glu Asn-COOH | HIF-1α regulated HRE (hypoxia response element) 5'-[AG]CGTG-3' //ACGCTCACGTGCT (−307–295) HIF-1α binding site in the gene of transcription factor NPA3. |
| 8 | 13aa Met Lys Glu Lys Ser Lys Asn Ala Ala Lys Thr Arg Arg-COOH | HIF-1α regulated HRE (hypoxia response element) 5'-[AG]CGTG-3' //ACGCTCACGTGCT (−307–295) HIF-1α binding site in the gene of transcription factor SIM2. |
| 9 | 9aa Lys Glu Lys Ser Lys Asn Ala Ala Arg-COOH | HIF-1α regulated HRE (hypoxia response element) 5'-[AG]CGTG-3' //acgctcaCGTGct (−307–295) HIF-1α binding site in the gene of transcription factor SIM2. |
| 10 | 13aa Met Lys Glu Lys Ser Lys Asn Ala Ala Arg Thr Arg Arg-COOH | HIF-1α regulated HRE (hypoxia response element) 5'-[AG]CGTG-3' //ACGCTCACGTGCT (−307–295) HIF-1α binding sites in the genes of transcription factors SIM1 and NPA3 |
| 11 | 9aa Lys Glu Lys Ser Lys Asn Ala Ala Arg-COOH | HIF-1α regulated HRE (HYPOXIA RESPONSE ELEMENT) 5'-[AG]CGTG-3' //ACGCTCACGTGCT (−307–295) HIF-1α binding site in the gene of transcription factor SIM |
| 12 | 9aa His Ser Glu Ile Glu Arg Arg Arg Arg-COOH | HIF-1α regulated XRE (XENOBIOTIC RESPONSE ELEMENT) 5'-acgctcaCGTGct-3' (−310–298) The binding sites of transcription factor HIF-1α in its downstream regulated gene |
| 13 | 5aa Glu Arg Arg Arg Arg-COOH | HRF-1α regulated XRE (XENOBIOTIC RESPONSE ELEMENT) 5'-acgctcaCGTGct-3' (−310–298) The binding sites of transcription factor HIF-1α in its downstream regulated gene |
| 14 | 13aa Ala Arg Glu Asn His Ser Glu Ile Glu Arg Arg Arg Arg-COOH | HIF-1α regulated XRE (XENOBIOTIC RESPONSE ELEMENT) 5'-acgctcaCGTGct-3' (−310–298) HIF-1α binding site in the gene of transcription factor ARNT |
| 15 | 9aa Lys Glu Lys Ser Lys Asn Ala Ala Arg-COOH | HIF-1α regulated XRE (XENOBIOTIC RESPONSE ELEMENT) 5'-acgctcaCGTGct-3' (−310–298) HIF-1α binding site in the gene of transcription factor ARNT |

TABLE 2-continued

The amino acid sequences and target sites of the chromatin peptides capable of blocking HIF-1α and its related transcription factor genes

| Chromatin peptide # | Amino acid sequnce | Target |
|---|---|---|
| 16 | 13aa<br>Ser Arg Glu Asn<br>His Ser Glu Ile<br>Glu Arg Arg Arg<br>Arg-COOH | HIF-1α regulated XRE (XENOBIOTIC RESPONSE ELEMENT)<br>5'-acgctcaCGTGct-3'<br>(−310−298)<br>HIF-1α binding site in the gene of transcription factor ARN2 |
| 17 | 13aa<br>Ala Arg Glu Ala<br>His Ser Glu Ile<br>Glu Lys Arg Arg<br>Arg-COOH | HIF-1α regulated XRE (XENOBIOTIC RESPONSE ELEMENT)<br>5'-acgctcaCGTGct-3'<br>(−310−298)<br>HIF-1α binding site in the gene of transcription factor BMAL |
| 18 | 9aa<br>His Ser Glu Ile<br>Glu Lys Arg Arg<br>Arg-COOH | HIF-1α regulated XRE (XENOBIOTIC RESPONSE ELEMENT)<br>5'-acgctcaCGTGct-3'<br>(−310−298)<br>HIF-1α binding site in the gene of transcription factor BMAL |
| 19 | 13aa<br>Lys Arg Val Ser<br>Arg Asn Lys Ser<br>Glu Lys Lys Arg<br>Arg-COOH | HIF-1α regulated XRE (XENOBIOTIC RESPONSE ELEMENT)<br>5'-acgctcaCGTGct-3'<br>(−310−298)<br>HIF-1α binding site in the gene of transcription factor CLOC |
| 20 | 13aa<br>Lys Arg Ala Ser<br>Arg Asn Lys Ser<br>Glu Lys Lys Arg<br>Arg-COOH | HIF-1α regulated XRE (XENOBIOTIC RESPONSE ELEMENT)<br>5'-acgctcaCGTGct-3'<br>(−310−298)<br>HIF-1α binding site in the gene of transcription factor NPA2 |
| 21 | 9aa<br>His Ser Glu Ile<br>Glu Lys Lys Arg<br>Arg -COOH | HIF-1α regulated XRE (XENOBIOTIC RESPONSE ELEMENT)<br>5'-acgctcaCGTGct-3'<br>(−310−298)<br>HIF-1α binding site in the genes of transcription factors NPA2 and CLOC |

The current studies suggest that these chromatin peptides can also block some transcription factors unrelated to glycolysis, inflammation and blood vessel growth stimulation or the necessary regulation pathway for normal cell proliferation and metabolism. For example, analysis on gene regulation elements contained in the upstream promoter has demonstrated that Hα promoter contains marrow-genetic branch gene MZF1 Trans-element, neuro-genetic HEN Cis-element, epithelial tissue-genetic TAP4 Cis-element, erythrogenic NFE2 Cis-element, and Blocking HIF-1α encoding gene may influence epithelial renewing and metabolism. Furthermore, similar results have been obtained in the analysis on Hα regulation network and its downstream related genes. However, lots of animal innocuity tests have shown the animal health and the growth and development of childhood mouse and adult rabbits are unaffected by the treatment of chromatin peptides to block HIF-1α gene of malignant cells, with the safety dose up to 5 mg/kg (about 6.25 times of human) (see practice Examples). The following may account for this as far as we are concerned. Firstly, HIF-1α is low-expressed or unexpressed in most adult tissues, only high-expressed in impaired tissues and is probably mainly related to the first aid of hypoxia for the adult individuals. Secondly, the arrangement pattern of transcription factors is network, not straight line, thus the proliferation; histogenesis and histometabolism of HIF-1α related cell not only involve HIF-1α regulation pathway but also others. Thirdly, the comparison between the chromatin peptides' homology domain of HIF-1α hypoxia-controlled branch elements HRE/XRE, vacuity-controlled branch C-MYC element RE(5'-CAC[GA]TG-3') and the demand-controlled branch-C-FOS in cell proliferation reveals that there is not enough homologization between HRE's natural Trans-chromatin peptides and C-MYC/C-FOS's peptides. Therefore, the Trans-chromatin peptides of the HIF-1α blocking pathway that we designed will not influence biological functions of C-MYC/C-FOS pathway, thus will not interfere the normal functions of cell renewing and differentiation regulated by direct or indirect communication.

Studies show the HIF-1α blocking induced by these chromatin peptides has high specificity towards malignant cells. Firstly, HIF-1α gene of normal cells are seldom blocked while the allel of malignant cells can specifically bind with these chromatin peptides, probably due to the highly condensation of DNA condition of HIF-1α encoding gene in normal cells, which makes it hard to bind to these chromatin peptides, while in malignant cells, the activated and unfolded DNA condition of HIF-1α encoding gene makes it easy to bind to these chromatin peptides. Secondly, there's no impacting binding site between the DNA area unrelated to transcriptional control gene HIF-1α network regulation both in the normal and malignant cells.

These chromatin peptides can be used simultaneously to block the transcription of Hα gene itself and Hα promoted transcription of over 40 functional genes, resulting in cell hypoxia responses (glycolysis, immuno-inflammation and anginogenesis), thus to block the malignant proliferation of malignant cells under in situ hypoxia condition and to block the HIF-1α pathway of inflammatory invasion to adjacent tissues and blood vessel metastasis to the whole body.

It is of great importance that these chromatin peptides only block the pathway of cell continuing proliferation/invasion/metastasis under hypoxia condition which specifically house the malignant cells, neither directly blocking the cell proliferation/cycle protein activation cascade necessary for tissue regeneration and proliferation, nor blocking the common transcription factor E2 element/E2F1 transcription factor, the promoter for cycle group gene transcription. Therefore, they are innocuous to normal health, but specifically block the proliferation/invasion/transfer of malignant cells and may serve as a potent for the medication of many kinds of carcinoma.

Human gene regulation network is so complicated that there will be a quite long time before the whole mechanism can be uncovered. With this consideration, the safety of the chromatin peptides is mainly determined by the specificity tests of target sites of chromatin peptide medicine cells and the animal tests.

These chromatin peptides only block the malignant proliferation/invasion/metastasis pathway of malignant cells. On the one hand, most malignant cells die from the shortage of energy and nutrition; on the other hand, the survived disordered HIF-1α regulated malignant cell clones from the differentiated cells maintain intact cells function or chromatin pathway of gene transcription regulation cascade for cell apoptosis and will transform to play a role in body functions. In the end, all the cells will experience natural apoptosis because of the limited life span of differentiated cells. For the malignant cell clones from stem cells, a small quantity of survived and differentiated cells stay in latency after HIF-1α blocking, maintaining division and differentiation ability and reoccurrence may happen when these chromatin peptides fall off from the blocked targets or cell division occurs. In that case, supplementation of Hα chromatin peptides is usually recommended to maintain a sustained blockage. For enteron, genital system and exteriority carcinoma, the lump can fall off and be discarded. However, in other cases, although the lumps may die after the medication, surgery and other treatments may be required to remove the lump if they are too large and interfere with the normal function of cells and tissues. For those larger tumor tissues, the combination of surgery and continued application with chromatin peptides to block the malignization pathway of survived malignant cells can be a hope to get the root in effective non-toxicant treatment towards all kinds of carcinomas.

PRACTICE EXAMPLES

The following examples are cited to exemplify the present invention.

Example 1

The polypeptides in the list numbered 1-21 were synthesized through solid phase peptide synthesis (SPPS), including adding amino acids protected by protecting group into the peptide chain, which was anchoring on the chemically stable granules, so as to disassociate peptides from reagent and solvent by simple filtering. After the synthesis, the chains were split from supporter and then conduct purification.

Example 2

Block HIF-1α gene self promoter HRE element and the chromatin peptide of HIF-1α transcription factor downstream promoter HRE element, that is, to block HRE element by trans-chromatin peptide 14 mer with the sequence of Arg Arg Lys Glu Lys Ser Arg Asp Ala Ala Arg Ser Arg Arg (SEQ ID NO: 2). The highly metastatic tumor HCT of human colon carcinoma cell line was inoculated into the forelimb armpit of BALB/c-nu, a kind of female nude mouse, with amount of 5 million tumor cells/per mouse. Five days later, the area of tumor cells implanted was directly treated by injection with the above-mentioned 14 mer peptide solution, by a dose of 5 mg/kg daily. The drug treatment group and control (saline) group were set up, with 25 mice in each side. The experiment mice were killed after 21 days, measuring the tumor weight. After weighing the tumor taken from each mouse, keep it in 4% formaldehyde. Paraffin section shed paraffin for 10 minutes through xylene, then deal with alcohol, stain in hematoxylin, and then stains with 0.5% eosine ethanol. After that, mount with neutral gum. Analyze under microscope and take films. The results are showing as FIG. 1(A) and FIG. 1(B).

$$\text{Inhibition ratio of tumor weight} = (1 - \frac{\text{the average tumor weight in treatment group}}{\text{the average tumor weight in control group}}) \times 100\%$$

$$= 86.4\%$$

There were four experiment mice in the treatment group with tumors totally disappeared.

Pathological section indicated that a lot of apoptotic bodies and cell debris were found in the central part of the tumor in the treatment group, while cancer cells still remained active growth around the verge of tumor. The drug didn't significantly change the weights of the animal, predicting small toxicity to the experiment animals. Observation of tumor tissue treated with chromatin peptide drug FIG. 1(B) comparing with control FIG. 1(A), as shown in FIG. 1(A) and FIG. 1(B).

Example 3

Block HIF-1α gene self promoter HRE/XRE element and the chromatin peptide of HIF-1α transcription factor downstream gene, that is, to block HRE element by trans-chromatin 10mer peptide of NH2-Arg Lys Glu Lys Ser Arg Asp Ala Ala Arg-COOH (SEQ ID NO: 5), and to block XRE element by cis-chromatin 9mer peptide of NH2-His Ser Glu Ile Glu Arg Arg Arg Arg-COOH (SEQ ID NO: 15). These two chromatin peptides can selectively shut down the cell hypoxia response path which the tumor cells must pass for malignant proliferation, infiltrate and transfusion, whereas normal cells needn't pass this way. Therefore, they were proper for inhibiting and preventing the recurrence of the illness for the patients with tumor and operation, thus realize a nontoxic curative effect.

The animal osteosarcoma cell line S-180 was inoculated into the forelimb armpit of the female "Kunming" nude mouse with weight range between 18-20 g, with amount of 2.5 million cells/per mouse. There were four groups, the high dose group (5 mg/kg), medium dose group (2 mg/kg), low dose group (0.5 mg/kg) and the control group, with 30 mice in each group. Administer injection to the tumor surroundings at the second day after inoculation. Administration was given daily. At the $5^{th}$, $10^{th}$ and $14^{th}$ day, judge the development of tumors by touching, and calculate tumor incidence rate. The experiment mice were killed at the $14^{th}$ day, measuring the tumor weight.

TABLE 3

Tumor incidence rate

| | groups | | |
|---|---|---|---|
| | $5^{th}$ day | $10^{th}$ day | $14^{th}$ day |
| Control | 67% | 93% | 100% |
| Low dose | 47% | 67% | 87% |
| Medium dose | 13% | 27% | 57% |
| High dose | 0% | 7% | 20% |

The tumor inhibition rate was calculated by the average tumor weight at the $14^{th}$ day. The rates were 94.4%, 69.5% and 34.5% for the high, medium and low group respectively. Statistics analysis showed that compared with the control group, there's great significant difference in the high and medium dose group (P<0.01), with significant difference in low dose group (P<0.05).

Example 4

The experiment blocking HRE element by trans-chromatin 10 mer peptide of NH2-Arg Lys Glu Lys Ser Arg Asp Ala Ala Arg-COOH (SEQ ID NO: 9) was performed by using a breast cancer animal model.

The human breast cancer cell line 0404 MDA-MB-435 was inoculated into the forelimb armpit of BALB/c-nu, a kind of female nude mice, with amount of 5 million cells/per mouse. The experiment animals with tumor size of 100-200 MM$^3$ were randomized into four groups, at the 14$^{th}$ day after inoculation of cancer cells. There were 16 mice in each group, treated with different doses of low (0.5 mg/kg), medium (2 mg/kg), and high (5 mg/kg). The control group was treated with normal saline. Administer injection to the tumor surroundings every day after inoculation. The growth tumor volume was measured every 3 days. All experiment mice were killed at the 21st day; tumor growth rate was measured by volume and weight.

TABLE 4

The volume of tumor sizes on average (CM$^3$)

| Group | 3$^{rd}$ day | 7$^{th}$ day | 10$^{th}$ day | 14$^{th}$ day | 17$^{th}$ day | 21$^{st}$ day |
| --- | --- | --- | --- | --- | --- | --- |
| Control | 2.002913 | 3.192501 | 4.957876 | 8.791081 | 9.005716 | 11.10098 |
| Low dose | 1.475294 | 3.312554 | 4.969706 | 7.668257 | 8.482121 | 8.953155 |
| Medium dose | 1.294934 | 2.133484 | 2.721365 | 4.878569 | 6.274266 | 6.119234 |
| High dose | 1.407653 | 1.461075 | 1.252597 | 2.211489 | 2.3635 | 1.793058 |

The above results indicated that the trans-chromatin 10 mer peptide of NH2-Arg Lys Glu Lys Ser Arg Asp Ala Ala Arg-COOH can inhibit breast cancer growth in the animal model.

The above results indicated that the trans-chromatin 10 mer peptide of NH2-Arg Lys Glu Lsy Ser Arg Asp Ala Ala Arg-COOH (SEQ ID NO: 9) inhibit breast cancer growth in the animal model.

Example 5

Patient with lung cancer existing carcinomatous metastasis to marrow conducted radiotherapy. Due to the broad range of other places, we adopted to block HRE element of HIF-1α regulated downstream genes by chromatin 14 mer peptide of NH2-Arg Arg Lys Glu Lys Ser Arg Asp Ala Ala Arg Ser Arg Arg-COOH (SEQ ID NO: 2). Intravenous injections were given every 5 days, with a dose of 2 mg each time, and one month as a course of treatment. In addition, antibiotics were accompanied to control complicated infection. Skeleton ache symptom decreased after five days, and osteodynia disappeared 20 days later, with cancer free three months later.

Example 6

Patient with small cell lung cancer, at middle and advanced stage, had micrometastasis to liver. Block HRE element of HIF-1α regulated downstream genes by chromatin 13mer peptide of NH2-Arg Lys Glu Lys Ser Arg Asp Ala Ala Arg Cys Arg Arg-COOH (SEQ ID NO: 4). Administer intravenous injection every 10 days, with 5 mg each time. 15 days later, dyspnoea and referred pain all vanished. Microscopily repeated test of sputum found no malignant cells falling off at the 90th day. And at the 100th day, biopsy found no malignant cells.

Example 7

Breast cancer were found in dogs, with tumor size of 45 mm×50 mm. NH2-Lys Arg Ala Ser Arg Asn Lys Ser Glu Lys Lys Arg Arg-COOH (SEQ ID NO: 20) was directly injected to the tumor, with 0.5 mg each time, and administration was given every 15 days. Tumor disappeared at 20th day.

Safety Test Using Animals

Safety Test 1

Acute Toxic Test of HIF-1α Pathway Impacting Peptides to Rabbits

Healthy rabbits with 1.5 kg-1.7 kg were recruited to groups, with 5 in each group. Intraperitoneal injection was given with dose of 0.5 g/kg body weight. The control group was only injected with normal saline solution. Measure the rectal temperature once every hour within 48 h. The result showed normal temperature.

Safety Test 2

Acute Toxic Test of HIF-1α Pathway Impacting Peptides to Mice

Healthy mice with 20-25 g were selected to groups, with 12 female and 12 female in each group. Mice in each group were intraperitoneal injected chromatin peptides 1-21, with 0.25 ml (0.5 mg) impacting medium, normal saline solution with the concentration of peptide 2 mg/ml, while for the control group, only inject normal saline. Seven days after injection, observe the changes in central nervous system, cardiovascular system, skin, hair, automatic nervous system, gastro intestinal system, mucosa, eyes, respiratory system and genital system. Measure the rectal temperature once every hour within 48 hours. The result showed that the temperatures were normal and there's no abnormality in each observe index among the treatment group and the control.

Safety Test 3

Chronic Toxicity Test of HIF-1α Pathway Impacting Medium to Rabbits

Healthy rabbits with 1.3 kg-1.5 kg were recruited to groups, with 5 in each group. Intraperitoneal injection was given with peptide 0.5 mg/ml concentration. The injected dose was 0.5 g/kg body weight. The control group was only injected normal saline. Injection was done once a day within 180 days. Observe the changes in central nervous system, cardiovascular system, skin, hair, automatic nervous system, gastro intestinal system, mucosa, eyes, respiratory system and genital system. Measure the rectal temperature once every hour within 48 hours. The result showed that there is no abnormality in each observe index among the treatment group and the control.

The invention claimed is:

1. An isolated peptide consisting of the amino acid sequence of SEQ ID NO:2.

* * * * *

SEQUENCE LISTING

<160> NUMBER OF SEQ ID NOS: 21

<210> SEQ ID NO 1
<211> LENGTH: 10
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 1

Arg Lys Glu Lys Ser Arg Asp Ala Ala Arg
1               5                   10

<210> SEQ ID NO 2
<211> LENGTH: 12
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 2

Lys Glu Lys Ser Lys Asn Ala Ala Arg Thr Arg Arg
1               5                   10

<210> SEQ ID NO 3
<211> LENGTH: 14
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 3

Arg Arg Lys Glu Lys Ser Arg Asp Ala Ala Arg Ser Arg Arg
1               5                   10

<210> SEQ ID NO 4
<211> LENGTH: 13
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 4

Arg Lys Glu Lys Ser Arg Asp Ala Ala Arg Cys Arg Arg
1               5                   10

<210> SEQ ID NO 5
<211> LENGTH: 10
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 5

Arg Lys Glu Lys Ser Arg Asp Ala Ala Arg
1               5                   10

<210> SEQ ID NO 6
<211> LENGTH: 13
<212> TYPE: PRT
<213> ORGANISM: Artificial sequence

```
<220> FEATURE:
<223> OTHER INFORMATION: Designed based on transcription factors
      binding on HRE 5'-[AG]CGTG-3' on trans-direction

<400> SEQUENCE: 6

Arg Lys Glu Lys Ser Arg Asn Ala Ala Arg Ser Arg Arg
1               5                   10

<210> SEQ ID NO 7
<211> LENGTH: 17
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 7

Arg Lys Glu Lys Ser Arg Asp Ala Ala Arg Ser Arg Arg Gly Lys Glu
1               5                   10                  15

Asn

<210> SEQ ID NO 8
<211> LENGTH: 13
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 8

Met Lys Glu Lys Ser Lys Asn Ala Ala Lys Thr Arg Arg
1               5                   10

<210> SEQ ID NO 9
<211> LENGTH: 9
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 9

Lys Glu Lys Ser Lys Asn Ala Ala Arg
1               5

<210> SEQ ID NO 10
<211> LENGTH: 13
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 10

Met Lys Glu Lys Ser Lys Asn Ala Ala Arg Thr Arg Arg
1               5                   10

<210> SEQ ID NO 11
<211> LENGTH: 9
<212> TYPE: PRT
<213> ORGANISM: Artificial sequence
<220> FEATURE:
<223> OTHER INFORMATION: Designed based on transcription factors
      binding on HRE 5'-[AG]CGTG-3' on trans-direction

<400> SEQUENCE: 11

Lys Glu Lys Ser Lys Asn Ala Ala Arg
```

<210> SEQ ID NO 12
<211> LENGTH: 9
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 12

His Ser Glu Ile Glu Arg Arg Arg Arg
1               5

<210> SEQ ID NO 13
<211> LENGTH: 5
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 13

Glu Arg Arg Arg Arg
1               5

<210> SEQ ID NO 14
<211> LENGTH: 13
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 14

Ala Arg Glu Asn His Ser Glu Ile Glu Arg Arg Arg Arg
1               5                   10

<210> SEQ ID NO 15
<211> LENGTH: 9
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 15

Lys Glu Lys Ser Lys Asn Ala Ala Arg
1               5

<210> SEQ ID NO 16
<211> LENGTH: 13
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 16

Ser Arg Glu Asn His Ser Glu Ile Glu Arg Arg Arg Arg
1               5                   10

<210> SEQ ID NO 17
<211> LENGTH: 13
<212> TYPE: PRT
<213> ORGANISM: Artificial sequence
<220> FEATURE:
<223> OTHER INFORMATION: Designed based on transcription factors

```
binding on XRE 5'-caCGTGct-3' on cis-direction

<400> SEQUENCE: 17

Ala Arg Glu Ala His Ser Gln Ile Glu Lys Arg Arg Arg
1               5                   10

<210> SEQ ID NO 18
<211> LENGTH: 9
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 18

His Ser Glu Ile Glu Lys Arg Arg Arg
1               5

<210> SEQ ID NO 19
<211> LENGTH: 13
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 19

Lys Arg Val Ser Arg Asn Lys Ser Glu Lys Lys Arg Arg
1               5                   10

<210> SEQ ID NO 20
<211> LENGTH: 13
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 20

Lys Arg Ala Ser Arg Asn Lys Ser Glu Lys Lys Arg Arg
1               5                   10

<210> SEQ ID NO 21
<211> LENGTH: 9
<212> TYPE: PRT
<213> ORGANISM: Artificial sequence
<220> FEATURE:
<223> OTHER INFORMATION: Designed based on transcription factors
      binding on XRE 5'-caCGTGct-3' on cis-direction

<400> SEQUENCE: 21

His Ser Glu Ile Glu Lys Lys Arg Arg
1               5
```